United States Patent
Walsh, Jr.

(10) Patent No.: US 8,365,463 B2
(45) Date of Patent: *Feb. 5, 2013

(54) METHOD AND APPARATUS FOR DESALINATION OF WATER AND EXTRACTION OF CARBON DIOXIDE FROM FLUE GAS VIA CONTROLLED AND VARIABLE GAS ATOMIZATION

(76) Inventor: William Arthur Walsh, Jr., Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/506,742

(22) Filed: May 14, 2012

(65) Prior Publication Data

US 2012/0294788 A1    Nov. 22, 2012

Related U.S. Application Data

(63) Continuation-in-part of application No. 13/200,008, filed on Sep. 15, 2011, now Pat. No. 8,176,676, which is a continuation-in-part of application No. 12/650,618, filed on Dec. 31, 2009, now abandoned.

(60) Provisional application No. 61/204,172, filed on Jan. 2, 2009.

(51) Int. Cl.
 *A01G 7/00* (2006.01)
 *A01G 31/00* (2006.01)
 *A01H 13/00* (2006.01)

(52) U.S. Cl. .............................. 47/1.4; 47/59 R

(58) Field of Classification Search ............... 47/1.4, 47/17, 59 R
See application file for complete search history.

(56) References Cited

U.S. PATENT DOCUMENTS

| 4,209,943 | A | * | 7/1980 | Moeller et al. | 47/1.4 |
| 4,314,670 | A | * | 2/1982 | Walsh, Jr. | 239/11 |
| 4,438,591 | A | * | 3/1984 | Kessler | 47/1.4 |
| 4,473,970 | A | * | 10/1984 | Hills | 47/1.4 |
| 2008/0086938 | A1 | * | 4/2008 | Hazlebeck et al. | 47/1.4 |
| 2010/0242355 | A1 | * | 9/2010 | Blotsky | 47/1.4 |
| 2010/0257781 | A1 | * | 10/2010 | Batty et al. | 47/1.4 |

* cited by examiner

*Primary Examiner* — Monica Williams
(74) *Attorney, Agent, or Firm* — Ira S. Dorman

(57) ABSTRACT

A water-desalination and carbon dioxide extraction method employs a greenhouse having a transparent, double-pane roof structure and containing an open-top receptacle for a receiving quantity of saline water or an aqueous mixture, derived from flue gas, of dissolved and suspended alkaline metal salts, which roof structure and receptacle are substantially coextensive and rectangular. A series of remotely controllable nozzles, capable of producing sheet-like discharges, withdraw the saline water or the aqueous mixture from the receptacle and discharges it into the overlying space for exposure to solar radiation passing through the roof structure, for controlled absorption of solar energy by the saline water or for effecting release carbon dioxide at elevated temperatures. Ambient air, heated during passage through channels in the transparent roof structure, may be used in a second greenhouse for promoting evaporation of free water or in other method steps.

1 Claim, 2 Drawing Sheets

METHOD AND APPARATUS FOR DESALINATION OF WATER AND EXTRACTION OF CARBON DIOXIDE FROM FLUE GAS VIA CONTROLLED AND VARIABLE GAS ATOMIZATION

CROSS REFERENCE TO RELATED APPLICATIONS

This application is a continuation in part of U.S. patent application Ser. No. 13/200,008, filed Sep. 15, 2011, now U.S. Pat. No. 8,176,676 which is a continuation in part of U.S. patent application Ser. No. 12/650,618, filed Dec. 31, 2009, now abandoned which in turn claims the benefit of U.S. Provisional Patent Application No. 61/204,172, filed Jan. 2, 2009, the contents of which applications are incorporated hereinto, by reference.

BACKGROUND OF THE INVENTION

Field of the Invention

This invention relates to a method and means of controlling the absorption of solar energy by a liquid contained in a greenhouse by means of varying the breakup and solar exposure of the liquid by linearly deforming, spraying or atomizing it in application to mass production and harvesting algae, desalination of water and extraction of carbon dioxide from flue gas.

The Current Needs

The worldwide discussion of the need for a practicable means of offsetting global warming by reducing emission of carbon dioxide has focused attention on sequestering the significant quantities of carbon dioxide released from coal fired power plants as the primary means of offsetting global warming. Considerable effort is currently underway, or under consideration, to develop methods of separating the carbon dioxide from the other constituents of the combustion flue gas. Its separation and collection requires its liquefaction for transportation or storage. One of the methods being studied, for sequestering the large quantities of $CO_2$ that would be collected, is to transport it to sites suitable for deep-earth drilling and long-term storage in known underground cavities using deep earth drilling. It is recognized to be a costly solution, however.

An alternative solution is to utilize the $CO_2$ by its absorption in the natural process of growing algae with sunlight. This method is currently under development in various stages ranging from laboratory studies and pilot scale tests to algae growing farms. The latter stage involves the use of large capacity growth beds, covering many acres, fed by sources of naturally growing algae culture plus nutrient-enriched solutions. These are blanketed with carbon dioxide enriched air under transparent canopies exposed to sun light. The growth rate of the algae is subject to the naturally varying conditions of sunlight and heat, as well as the varying and limited depth-penetration, into the nutrient solution, of the solar rays and carbon dioxide. Methods currently used to offset the growth limiting factors involve solution stirring, including paddle-wheel mixing, and bubbling of the air-$CO_2$ mixture up through transparent (glass) columns of algae solution. The growth also requires alternating periods of darkness and light exposure. Improved means of controlling the several variables that effect growth can serve to increase process efficiency and cost-effectiveness.

The prevalence of micro-algae growth in coastal sea waters has adversely affected the economies of marine industries, e.g., the destruction of dam beds by "brown tides." A low cost method of collecting, concentrating and harvesting the algae can overcome the problem.

The increasing shortages of water in developing countries point to the need of sources of desalinated sea water. Current methods of producing potable water by distillation or osmosis are costly in terms of both capital and operating expense. A low cost method that includes solar energy evaporation and condensate collection can provide a world-wide benefit.

Investigations have been undertaken of the feasibility of absorbing carbon dioxide from flue gas into aqueous mixtures of reactive chemicals. Considerable interest has been shown in its well known reaction with magnesium hydroxide slurry to form the carbonates. By subsequently heating the reaction-product mixture, concentrated carbon dioxide is evolved and collected.

The magnesium hydroxide slurry is then recycled for reuse. A proposed means of employing this reaction in flue gas cleaning has involved the use of a conventional wet-scrubber for the absorption, followed by circulating the slurry to a steam heated reaction vessel to drive off the $CO_2$. Major questions pursuant to its industry adoption include the reaction time required for absorption and the energy required to extract the $CO_2$.

Background Technical Support

An element of the apparatus utilized in the current invention employs the method and teachings of expired patent, "Variable Gas Atomization," which was issued to this inventor on Feb. 9, 1982, (Reference 1). As utilized herein, variable gas atomization (VGA) refers to the method and designs of compressed air atomizing nozzles as described in Reference 1 and as described in modified form in Reference 2. Specifically, it refers to the use of nozzles that linearly deform the internally flowing liquid into a thin, flat sheet. This is done by employing cantilevered dividing walls that are deflected by the pressure difference between the liquid and compressed air to form thin liquid sheets of variable thickness, and typically ranging from somewhat less than 0.001" to 0.010" (25 to 250 microns). By varying the pressures and quantities of either the liquid of the compressed air flowing on both sides of the liquid sheets as the air and water pass through a converging, linear nozzle exit, the exiting sprays may be varied in form from that of flat sheets that break up into coarse droplets as they settle to that of more finely atomized droplets. The range of variation of sheet thickness and ultimate droplet size depends upon the thickness and cantilevered length of the walls dividing the liquid and air feed channels, and the range of pressure difference variation.

REFERENCES

1. Walsh, Jr., William A., "Variable Gas Atomization," U.S. Pat. No. 4,314,670, Feb. 9, 1982
2. Ellison, William, Ellison Consultants, Monrovia, M D, William A. Walsh, Jr., VGA Nozzle Company, Manchester, N H, Prof, Dr. Adnan Akyarli, Managing Director AKOKS, Izmir, Turkey and Prof. Dr. Aysen Muezzinoglu, Pres. TUNCAP, Izmir, Turkey, "Commercial Application in High Efficiency FGD of Sorbent Injection with Flue Gas Humidification," Sixteenth Annual International Pittsburgh Coal Conference, Oct. 11-15, 1999, Pittsburgh, Pa.

SUMMARY OF THE INVENTION

In accordance with the present invention a method and apparatus are provided to control the utilization of solar energy by means of a variable form and controllable degree of atomization. They are utilized to promote and optimize the mass production of micro-algae together with its collection as an industrially applicable dewatered product, to produce desalinated water for industrial applications, and to extract $CO_2$ from flue gas.

DESCRIPTION OF THE PREFERRED EMBODIMENTS PERTAINING TO THIS INVENTION

Algae Production

Figure 1:
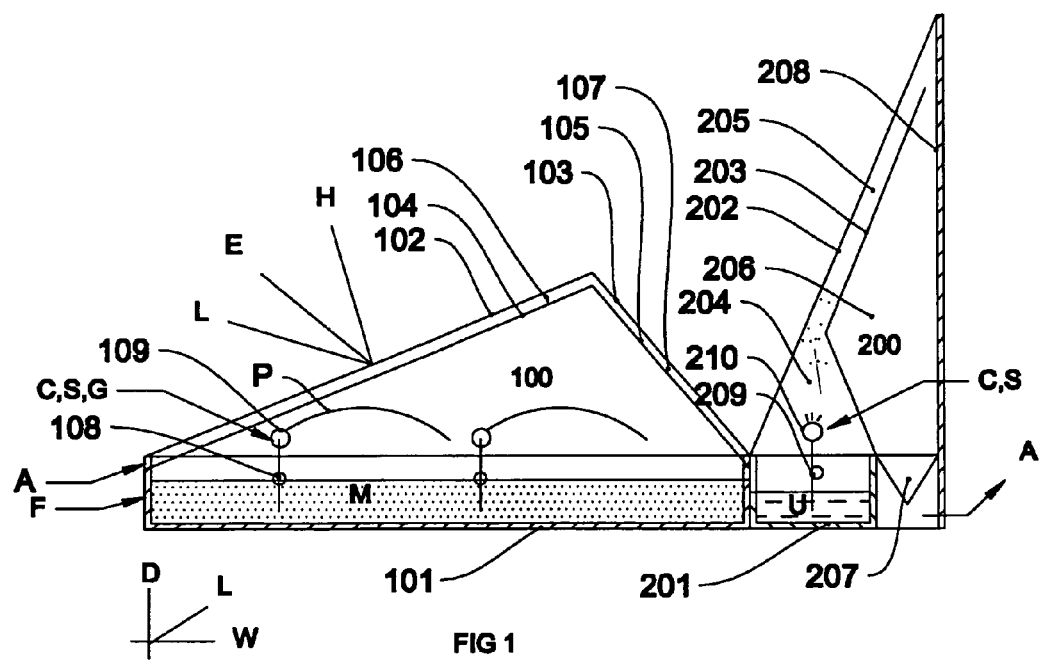
FIG. 1 is a cross-section view of a system including two adjoined greenhouses comprised of beds containing liquids with transparent panel covers set at angles relative to the solar latitude and seasonal angle suited to the particular operations described herein.

FIG. 1 shows an assembly of two adjoined greenhouses, generally designated as items 100 and 200, as typically employed herein for the solar production and solar harvesting of micro-algae and/or desalination. Greenhouse 100 is used for growing and concentrating micro-algae. Greenhouse 200 is used for harvesting the algae by atomizing its concentrated dispersion and evaporating the fine droplets to dryness plus collection of algae, together with dried nutrient and salts, by filtration. Pertinent features of greenhouse 100 include algae-suspended nutrient solution mixture M, algae-containing solution bed 101, of width W, depth D and length L, outer roof coverings 102 and 103, and inner roof coverings 104 and 105. Algae bed depth D is generally shallow and of the order of 2 to 4 feet so as to not produce the extended period of light exclusion that results with increasing depths. Width W is selected to suit construction costs and, as illustrated, would generally be of the order of 30 to 70 ft. Length L is proportional to the scale of algae production. It could be comprised of individual section lengths of the order of 100 feet, more or less, and could extend to cover many acres. Other ratios of length to width may be chosen to suit the available terrain. Outer roof coverings 102 and 103 and inner roof coverings 104 and 105 consist of two layers of transparent panels (such as glass or plastic) separated by spaces 106 and 107 to allow passage of air. Roof coverings 102 and 104 are oriented in a southerly direction (in northern latitudes) and tilted at a suitable angle in order to generally maximize the transmission of solar energy.

Dilute algae-water suspension feed F is drawn from a naturally growing source (pond, stream or sea bed), screened of foreign matter and delivered into one side of the growing bed (or bed section) at intervals along its extended length. Production may also be initiated by feeding from specific laboratory grown strains of algae. Growth promoting nutrients N are added to feed F as needed. Algae-nutrient mixture M is drawn continuously from bed 101 by metering pumps 108 and delivered to linear VGA nozzles 109 where it is atomized for exposure to solar energy and carbon dioxide enriched air. Mixture M issues from linear VGA nozzles 109 in the form of thin, extended plume P issuing mostly in the form of thin sheets that break up into coarse spray droplets that quickly settle into bed 101 after a brief exposure to solar energy. The nozzles are operated in a mode to specifically produce coarse atomization, and are designed with features that enable considerable variation in sheet thickness and droplet size. By varying the degree of liquid break-up, the exposure to solar flux is controlled and varied so as to maximize the growth rate as the solar energy varies. Moderately compressed (generally in the range of 5-30 psig.) atomizing air C and secondary, blower air S are delivered to nozzles 109 to assist in the formation and control of the degree of atomization of liquid into spray plume P issuing from the nozzles. Additional, tertiary gas mixture G, consisting of air and $CO_2$, (such as flue gas) at approximately ambient pressure, may be delivered separately through nozzles 109 to mix with plume P. $CO_2$ may be added to air flows C and S to provide intimate contact with spray droplets. Nozzles 109 are placed at intervals along length L of the bed. As illustrated, mixture M flows slowly across the bed to exit on the opposite side and flow into adjoining greenhouse 200 as the ultimate, maximum-concentration, mixture U. Depending on the ratio of L to W, the flow of mixture M could alternatively be in the length direction. Additional nozzles are placed at intervals across the bed to further promote algae growth as its concentration increases. The number of VGA nozzles required is also a function both the bed width and length. Ambient air A is drawn into air spaces 106 and 107 by an external induced draft blower, to be solar-heated as it flows across the bed, and is thence delivered into greenhouse 200. Atomizing air flows, C and S, plus gas mixture G, warmed and humidified in greenhouse 100, flow into greenhouse 200 to merge with heated ambient air A. The small portion of fine droplets in plume P that have not settled back into bed 101 is carried with it. Inasmuch as the efficiency of photosynthetic absorption of solar energy is relatively low (generally estimated at 11% maximum), the flow of ambient air A through spaces 106 and 107 serves to absorb excess solar energy, thereby preventing overheating of greenhouse 100 and bed 101. If additional heat removal is required, algae mixture M can be externally circulated through a simple pipe-array, external water spray heat exchanger.

Maximizing the growth rate and concentration of algae requires control of the temperature of mixture M in bed 101, preferably to within the range 68° F. to 72° F. It also requires that the droplet size and solar exposure time of spray P be controlled and varied as needed to promote optimum growth while the algae culture continues to increase in concentration. Since growth of algae is a function of the relative periods of light and darkness, successive exposures to sun light, air and $CO_2$ through repeated spraying, variation of the quantities sprayed and variation of depth D of the algae bed are utilized to promote maximum growth rate and algae concentration. The effect of the relative humidity of the atmosphere in contact with sprayed algae depends upon the droplet size, droplet exposure time and the algae specie. Since a relative humidity above 85% is generally preferred, it is desirable to limit the influx and exit of air in the greenhouse space used for the algae spraying and solar exposure.

Pertinent features of greenhouse 200 include algae bed 201, containing concentrated algae mixture U, roof covering 202, interior divider 203, atomization space 204, heating and evaporating space 205, particle settling space 206, bag type solids collector 207 and rear structural wall 208. The rear wall is preferably finished with a light reflecting interior surface. Concentrated algae mixture U is delivered by pumps 209 to linear VGA nozzles 210, which utilize compressed air C (generally compressed to the range of 30 to 70 psig.). Nozzles 210 are generally similar to nozzles 109 (without the provision for adding air-$CO_2$ mixture), but are designed specifically for fine atomization. With adjustment features that allow considerable variation in both droplet size and flow rate, maximum evaporative drying can be produced during exposure to the available solar energy. Solar-heated ambient air A, flows into atomization space 204 and mixes with air issuing from nozzles 109 and 210, plus residual, unabsorbed $CO_2$, then flows upward through drying space 205 carrying the finer droplet size portion of the spray produced by nozzles 210, plus any carry-over from nozzles 109. The upward flow of air and spray droplets causes a fractionation of the generally broad distribution of droplet sizes produced by an air atomizer, with the finer fraction being lofted upward. The remaining droplets (generally larger mass-fraction of the droplets in the distribution of droplet sizes within a spray) fall back to the bed to be re-atomized. Air stream A, thence flows out of the top of the drying space and downward carrying the dry particulate for collection in bag type filters 207. Air stream A, humidified by evaporation of water from droplets during drying, flows from filter 207 out of greenhouse 200 to a heat exchanger consisting of a pipe array cooled by an external spray of water delivered from a natural water source. Condensate from the heat exchanger is collectible as desalinated water. Air flow through the greenhouse enclosures is produced by an induced draft fan following the heat exchanger.

Any dissolved salts present in the algae suspension will be collected together with the dried algae in greenhouse 200. This may be undesirable, particularly with marine algae where the salt concentration exceeds that of the algae. In such case, an alternative method of operation may be employed. By first delivering the concentrated algae from greenhouse 100 to an algae separation step such as centrifuging, the separated solution may then be desalinated in greenhouse 200 for salt and/or remaining nutrient salts collection.

The sizes of the greenhouses required are estimated from available published data on algae growth, as follows:

| Algae Growing Greenhouse | |
|---|---|
| Solar Energy (U.S. 24 hour daily average): | 22 W/ft$^2$ = 1.25 Btu/minute/ft$^2$ |
| Efficiency of Photosynthesis: | 7.7% = 70% of 11% theoretical max. |
| Energy Required for Photosynthesis: (6 mols $CO_2$ = 1 mol Algae) | 114.3 kCal/mol $CO_2$ = 3811 kCal/kg = 6860 Btu/lb Algae |
| System Unit Design Basis: | 1 gpm of aqueous suspended algae mixture harvested |
| System Unit, Harvested Algae Concentration: | 2% by wt. = .167 lb/min. = 10 lb/hr. |
| System Unit Solar Panel Area for Algae Growth at 10 lbs/hr and at 7.7% Efficiency: | 68600/1.25/60/.077 = 11900 ft$^2$ |

| Algae Harvesting Greenhouse | |
|---|---|
| To evaporate 1 gpm of water into air heated to 140° F., sat'd., from 70° F., sat'd: | 1247 Btu/lb evaporated or 10400 Btu/gal. |
| The quantity of air involved: | 7.267 lb air/lb water or 800 ft$^3$/gal |
| Unit Solar Panel Area for Algae Harvest: | 10400 Btu/gal/1.25 Btu/min/ft$^2$ = 8300 ft$^2$ |

Combined Greenhouse Growing and Harvesting

To completely evaporate finely atomized droplets requires a heated air stream of volume and velocity sufficient to loft them up through the drying space without their settling by gravity before drying and collection of the suspended solids. Since this, carrier-air volume is significantly larger than that required to contain the evaporated water, additional solar panel area must be provided for heating the carrier air. In the present system design, the additional air volume needed to loft the finely atomized droplets is pre-heated by absorbing the 92% of solar energy not utilized in algae growth. This is accomplished by providing the separate air passageway through the double solar panel roof on the algae growing greenhouse. The flow of air in the air passageway above the culture bed serves the added purpose of preventing overheating of the bed by absorbing the excess solar heat that is not utilized in growth. For convenience in construction and operation, the adjoining beds are made equal in length. The required bed sizes, based upon equal solar panel sizes is estimated by the following simplified heat balance equation based on 1 gpm algae mixture feed:

$$Q_S = Q_F + Q_G + Q_A$$

$$Q_S = Q_E + Q_H$$

$Q_S$=Solar energy available=1.25 Btu/ft$^2$×$A_p$, where $A_p$=panel area, ft$^2$/gpm $Q_F$=Heat to warm the feed=$w_f$×$C_p$×(70° F.−$t_f$), where $t_f$=feed temp., $w_f$=8.34 lb/gal feed, $C_l$=specific heat of liquid=1.0 Btu/Ib/deg. F., and $t_f$=algae feed temp.assumed=60° F.

$Q_G$=Heat absorbed in algae growth=6860 Btu/lb×0.167 lb/min=1146 Btu/min $Q_A$=Heat for added air and $CO_2$=$w_1$×$C_a$×($t_i$−70° F.), where $C_a$=specific heat of air=0.25 Btu/lb/deg. F.

$w_1$=$w_a$, lbs/min of ambient air+$w_{n1}$, estimated at 3 lbs/min, air and $CO_2$ added with nozzles in algae growing greenhouse $t_i$=the intermediate temperature to which to which added gases entering harvest bed are heated $Q_E$=Heat to evaporate fine droplets=10400 Btu/gal $Q_H$=Heat added to additional air provided to carry droplets=$w_2$×$C_p$×(140° F.−$t_i$), where $w_2$=$w_1$+$w_{N2}$, estimated at 40 lbs/min., nozzle air added for fine atomization.

With the solar panel areas of the two greenhouses designed to be of equal length, and set at 12,000 ft$^2$ each, and the panel widths assumed to be 40 ft, the bed lengths are 300 ft. Allowing a 6" channel width of the air drying passageway, it is estimated that an air flow rate of about 10000 ft$^3$/min will carry droplet of 25-30 microns diameter. Under these conditions, the air will be preheated to around 140° F. The combined footprint area of the two green houses is approximately 83% of the solar panel area or 20,000 ft$^2$.

In order to accommodate the extended bed length, a multiplicity of miniaturized, small flow capacity, VGA nozzles are employed. These are mounted in pipe-lance type enclosures suitably spaced at intervals along the bed. The lances are fed by pumps that draw the algae suspension from locations in the bed selected to maximize circulation of the mixture.

The solar energy unused, and thereby wasted, in photosynthesis is utilized for preheating the drying air. This significantly reduces the solar panel area for harvesting that would otherwise be required for heating the air volume needed to fractionate the droplet size distribution and convey the finer droplet sizes. Alternative methods of evaporating the large amount of water carried with the algae suspensions (typically concentrated to only 2% in current production practice) inherently involve considerable, costly energy.

Desalination

It is noted that essentially the same greenhouse configuration as illustrated in FIG. 1 may also be employed for desalination. In such case, the greenhouse identified as 100 is used to preheat the salt water and air used to loft the fine droplets for evaporation in greenhouse 200. It may also be used with brackish and waste water. In all desalination applications, the feed water is first filtered to remove undesirably large particulate. In the alternative, desalination mode of operation, greenhouse 100 is utilized to preheat both air and sea water prior to evaporation in greenhouse 200. Condensation of the evaporated water is accomplished by cooling the moisture laden air by passage through an array of pipes externally cooled by spraying with the same, ambient temperature water source as for desalination. It is recognized that the efficiency of external spraying depends not only on the water temperature but also on the ambient air temperature and humidity. However, since the heat transfer is a function of the ambient wet bulb temperature, it requires less surface pipe surface area than does a conventional shell and tube heat exchanger, which, in fact, is considered to be impractical in this application.

Based on a similar heat balance for the same greenhouse design, the desalination capacity is estimated at 6 gpm per acre.

Carbon Dioxide Extraction

Figure 2:
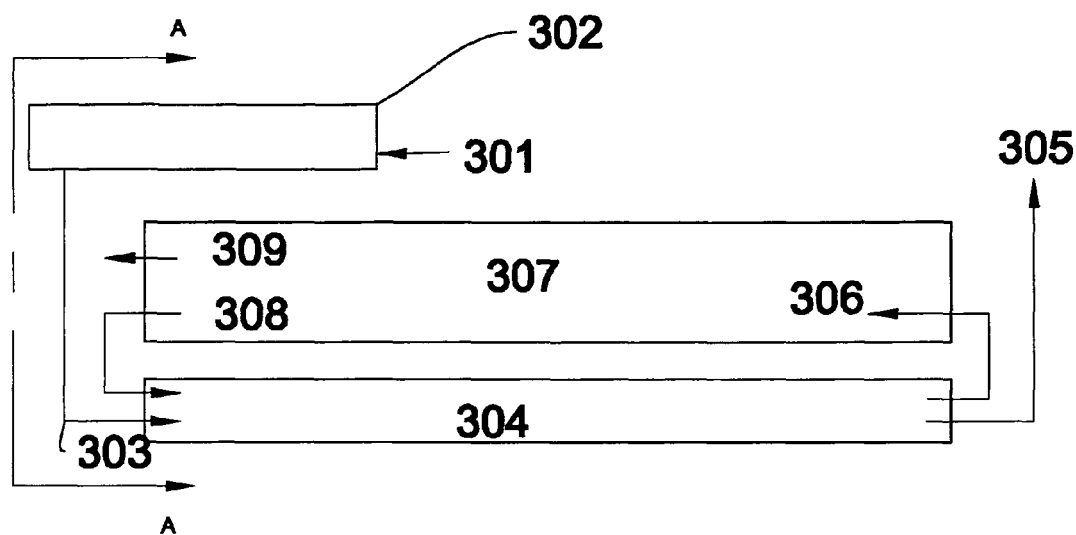
FIG. 2 shows plan and elevation views of a system including a modified flue gas duct comprised of a bed containing a re-circulated liquid for absorbing $CO_2$ and an associated greenhouse for solar extraction of the absorbed $CO_2$.
Figure 2:
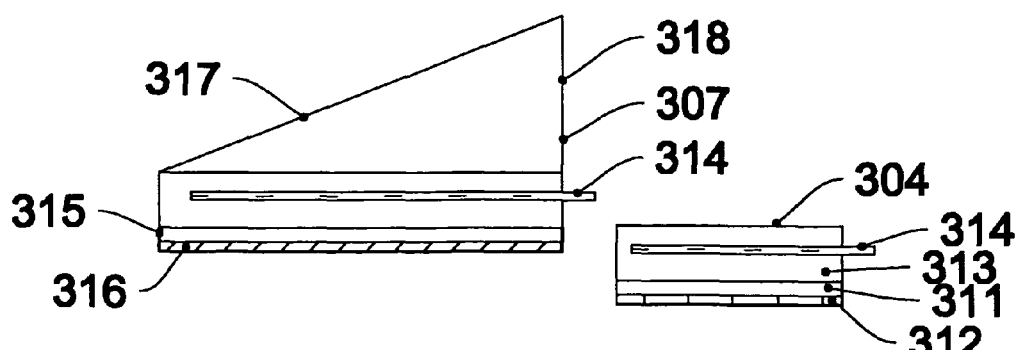

FIG. 2 shows a plan view and elevation view, A-A, of an assembly of a modified flue gas duct and a greenhouse, generally designated by the 300 series of numerals, as employed herein for extraction of $CO_2$ from flue gas. Flue gas 301, after scrubbing to remove $SO_2$, $NO_x$ and mercury must be cooled, preferably to below about 125° F. This may be done by externally spray cooling or submerging in a stream or other water source a section of duct 302. Pre-cooled flue gas 303 then passes into modified flue gas duct 304 fitted with bed 311 containing scrubbing medium 312. Although, as herein suggested, medium 312 would consist of magnesium hydroxide, $Mg(OH)_2$, slurry because of its apparent reasonable price and availability as a waste product, other chemicals could also be considered. Medium 312 is repeatedly sprayed into flue-gas-containing duct space 313 with linear, variable gas atomizing nozzles installed in nozzle-lances 314. The length of duct 304 provides the time needed for the $CO_2$ to diffuse into the extended liquid surface area but a means of dissipating the heat of reaction evolved between and $CO_2$ in forming magnesium carbonates. The liberated heat may be absorbed either by externally spraying the duct or by submerging in a stream or other water supply. Cleaned flue gas 305 is released to the atmosphere. Reacted slurry 306 is circulated into greenhouse 307 fitted with bed 315 containing circulating slurry 316. Additional nozzles 314 repeatedly spray slurry 316 into air space 317 where energy received through solar panel 318 furnishes the heat needed to reverse the reaction and release $CO_2$. Restored $Mg(OH)_2$ slurry 308 is recirculated back to duct 304 for reuse. Released $CO_2$ 309, together with the $H_2O$ involved in the reaction is delivered for collection.

The greenhouse size required to extract the $CO_2$ absorbed by the VGA induct spray-scrubbing method is estimated as follows:

Reversible reaction: $Mg(OH)_2 + 2 CO_2 \leftrightarrow Mg(HCO_3)_2$
Heat of Reaction with $CO_2$=375 Btu/lb $CO_2$, exothermic
Heat of Reverse Reaction=" ", endothermic
Carbon Dioxide @ 14% of Flue Gas=2200 lb/hr/MW
Solar Energy Available: 22 W/ft²=75 Btu/hr/ft²
US daily average hours of sunlight=4 hrs.
Solar Panel Area Required for 100% $CO_2$ extraction:
2200×375/75×24 hrs/day/4 hrs, avg.=66,000 ft²/MW or 1.5 acre per MW
At 16.7% $CO_2$ removal, or 4 hr/day operation, ¼ acre per MW is required.
The slurry absorption bed required is estimated to be about the same size.

These and all such other variations which would be obvious to one skilled in the art are deemed to be within the spirit and scope of the appended claims where expressly limited otherwise.

Having thus described the invention, what is claimed is:

1. A method of desalination utilizing solar energy to evaporate the water content of sea water, brackish water or other saline water solutions such as industrial waste water comprising:

providing a greenhouse that is generally rectangular, viewed in plan, and having roof structure that is also generally rectangular, that is transparent to solar radiation, and that is of double-pane construction to define at least one channel through which ambient air can pass to be heated by absorption of solar energy, the greenhouse containing open-top containment means, comprised of at least one receptacle, for the containment of a substantially continuous liquid bed and having an inlet adjacent one end and an outlet adjacent an opposite end, the containment means being spaced a substantial distance beneath the transparent roof structure and extending along substantially the full length and width thereof, with the greenhouse defining an enclosed space thereabove;

introducing into the containment means a quantity of saline water to provide a bed that fills the containment means, and that extends at least along substantially the full length of the containment means;

at least periodically adding to the containment means at the inlet a fresh supply of said saline water and withdrawing at the outlet a volume of said saline water that has been heated by exposure to solar energy entering the greenhouse;

repeated or continuously drawing quantities of said saline water from a subsurface region of said bed and spraying said quantities of saline water into the enclosed space, at numerous locations spaced longitudinally from one another, using a multiplicity of nozzles that are constructed to enable characteristics of the spray discharge to be varied by means controlled remotely from the nozzles, the nozzles effecting discharge of said saline water from positions above said bed surface and in the form of thin, substantially flat sheets that are oriented substantially horizontally or at a small angle of inclination relative to the horizontal, thereby facilitating the control of absorption of solar energy by the bed;

heating, by exposure to solar energy, the contents of the bed preferably to a temperature in the range of 120-140 degrees F.;

causing ambient air to flow through the at least one channel of the roof structure so as to permit said air to absorb a substantial portion of the solar radiation impinging on the roof structure and thereby to produce a supply of heated air, preferably, in the range of 120-140 degrees F., exiting therefrom;

providing a second greenhouse for further evaporating the water content of said saline water by absorption of solar energy, the at least one channel of the roof structure of the first mentioned greenhouse being operatively connected to the second greenhouse for the delivery of said supply of heated air thereto;

the second greenhouse having a double-pane roof structure similar to that of the first green house with said roof structure vertically oriented with 60 to 90 degrees relative to the horizontal;

the second greenhouse having an enlarged air space below the vertically oriented roof structure, with the air space extending the full horizontal length of the vertically oriented roof structure and widened sufficiently to permit the installation and operation of a series of spray nozzles, and with a bed beneath the roof structure extending the full length and width of the base of the vertically oriented greenhouse; and the second greenhouse containing a multiplicity of finely atomizing spray nozzles supplied by the saline water delivered from the first greenhouse, and wherein said supply of heated air is employed for lofting droplets discharged from the multiplicity of finely atomizing spray nozzles, from which no more than 50 percent by weight of such discharged droplets having diameters larger than about 50 microns.

* * * * *